United States Patent
Dharmadhikari et al.

(10) Patent No.: US 8,187,633 B2
(45) Date of Patent: May 29, 2012

(54) CONTROLLED RELEASE COATED TABLETS HAVING PROLONGED GASTRIC RETENTION

(75) Inventors: Nitin Bhalachandra Dharmadhikari, Mumbai (IN); Yashoraj Rupsinh Zala, Mumbai (IN)

(73) Assignee: Sun Pharma Advanced Research Company Limited, Mumbai (IN)

( * ) Notice: Subject to any disclaimer, the term of this patent is extended or adjusted under 35 U.S.C. 154(b) by 970 days.

(21) Appl. No.: 12/092,632

(22) PCT Filed: Nov. 3, 2006

(86) PCT No.: PCT/IN2006/000441
§ 371 (c)(1),
(2), (4) Date: May 5, 2008

(87) PCT Pub. No.: WO2007/072495
PCT Pub. Date: Jun. 28, 2007

(65) Prior Publication Data
US 2008/0241238 A1    Oct. 2, 2008

(30) Foreign Application Priority Data

Nov. 3, 2005  (IN) .................... 1373/MUM/2005

(51) Int. Cl.
*A61K 9/24* (2006.01)
*A61K 9/20* (2006.01)
*A61K 9/36* (2006.01)

(52) U.S. Cl. ......... 424/473; 424/468; 424/465; 424/480

(58) Field of Classification Search .................. 424/465, 424/468
See application file for complete search history.

(56) References Cited

U.S. PATENT DOCUMENTS 6,797,283 B1 * 9/2004 Edgren et al. ................. 424/472
2003/0232081 A1  12/2003 Doshi et al.
2005/0100602 A1  5/2005 Sako et al.

FOREIGN PATENT DOCUMENTS

| EP | 1 382 331 A1 | 1/2004 |
| EP | 1 568 361 A2 | 8/2005 |
| WO | 2003 101431 A1 | 12/2003 |
| WO | WO 2005039481 A2 * | 5/2005 |
| WO | WO 2007072495 A2 * | 6/2007 |

OTHER PUBLICATIONS

Dictionary, Povidone: definition of povidone and synonym of povidone [Downloaded May 18, 2011] [Retrieved from internet <URL: http://dictionary.sensagent.com/povidone/en-en/>], (5 pages).*
International Search Report of PCT/IN2008/000441, date of mailing Jul. 12, 2007.

* cited by examiner

*Primary Examiner* — Tracy Vivlemore
*Assistant Examiner* — Miriam A Levin
(74) *Attorney, Agent, or Firm* — Westerman, Hattori, Daniels & Adrian, LLP

(57) ABSTRACT

The present invention relates to a tablet composed of a core and a coating; said core is formed by two or more layers, wherein at least one of them contains an active agent (3). Wherein one of said layers is formulated as a swellable composition (2), the other one (4) is composed of inert compounds retaining its size at least until the coated tablet is emptied from the stomach. The coating composition is selected from the group comprising water insoluble polymers, ph dependent polymers or mixtures thereof. The active agent is released after rupture of the coating.

10 Claims, 1 Drawing Sheet

CONTROLLED RELEASE COATED TABLETS HAVING PROLONGED GASTRIC RETENTION

This application is a national stage application under 35 USC 371 of PCT/IN06/00441 filed Nov. 3, 2006, and claims priority to a foreign application number 1373/MUM/2005, filed in India on Nov. 3, 2005, the entire disclosures of which are incorporated herein by reference.

The present invention relates to controlled release coated tablets that are retained for longer period in the stomach.

BACKGROUND OF THE INVENTION

The art is replete with many references relating to drug delivery systems that when orally administered are retained in the stomach. Several such systems disclosed in prior art relate to retention of system in the stomach because the size of the system is large and thereby gastric emptying is delayed.

Prior art systems that provide a control on the release of the drug and also are retained in stomach because of their size and shape have certain drawbacks. The major drawback of a large majority of the disclosed prior art systems that have become commercially useful is that they are not sufficiently large in size initially but attain their size by swelling to several times their initial size this entails a risk that the system would be emptied from the stomach before it swells. This drawback has been overcome to an extent by systems that swell rapidly, however such systems must include enough quantities of swelling agents that swell rapidly but despite the internal swelling pressure created must not disintegrate earlier than desired. These requirements make the formulator's task difficult. There may be further limitations in formulation options for the formulator because the drug-containing matrix should release drug at a desired controlled release rate while also retaining its size. For example, this may be difficult when the dose of the active ingredient is large and relatively smaller quantities of pharmaceutical excipients suffice to provide the controlled release. A matrix so formed containing higher proportions of active ingredients as compared to other pharmaceutical excipients often erodes or disintegrates into parts earlier than desired for gastric retention. For example, systems disclosed in U.S. Pat. No. 4,777,033 (Patent '033) were found to have a drawback in that they did not remain intact when subjected to agitation in an aqueous medium. On the other hand, systems that are designed to avoid erosion or disintegration may be eliminated in the stools in an intact form, which raises apprehensions in the patient about the quality of the tablets or that he did not absorb the active ingredient.

There remains a need for a drug delivery system that provides an independent controlling mechanism for providing a slow delivery of the active ingredient and an independent controlling mechanism for providing size and rigidity and retaining size so as to be retained in the stomach over the desired period of release and which system is completely eroded or disintegrated in the intestine.

We described a novel drug delivery system in WO 2005/039481 (herein after referred to as '481publication), now U.S. application Ser. No. 10/572,502 published as US 2007/0071816 on Mar. 29, 2007, which is incorporated herein by reference. This patent application describes a novel oral drug delivery system that comprises a core with drug composition and a coating surrounding said core. In one embodiment, the coated tablet was designed to include a design feature comprising a swellable composition adjacent to a preselected surface of the coating. On imbibing water, the swellable composition swells and exerts pressure on the coating, particularly at the preselected surface, and the coating from only that preselected surface is removed. At the same time, the coating maintains its physical form and rigidity on other surfaces of the system to form a cup-shaped platform. The system was designed such that coating from one or more of the preselected surfaces was removed, and drug release occurred from the exposed surface. The exposed surface area remains constant over the periods of release and the drug was released at a uniform or zero-order rate from the system.

However, we have found that the oral drug delivery system of '481 can be modified to provide systems of the present invention in the form of coated tablets that are suitable for gastric retention and overcome the aforesaid drawbacks of the prior art gastric retention systems. The coated tablets of the present invention have an initial size and rigidity that is retained at least along one dimensions of the tablets and along at least one more dimension the size and rigidity is retained partially when the tablets are subjected to agitation in an aqueous medium. In other words, at least along one dimension the original size is retained and along a second dimension the size decreases as the components of the coated tablets erode or dissolve until an intermediate size is achieved and thereafter the coated tablets do not substantially erode or dissolve in the gastric fluids. The intermediated size tablet remnant can be emptied from the stomach without gastric obstruction, and in the intestine it can disintegrate or erode or dissolve.

SUMMARY OF THE INVENTION

The present invention provides a coated tablet having prolonged gastric retention comprising
- A. a core comprising two or more compositions in the form of compressed layers wherein at least one composition comprises a therapeutically active ingredient and rate controlling excipients
- B. a coat rupturing system comprising
  1. one of aforesaid composition in the form of a swellable compressed layer comprising a swelling excipient
  2. a coating comprising a film former adjoining said swellable compressed layer and surrounding said core, wherein the coating ruptures from at least one of the surfaces when the coated tablet is in an aqueous environment
- C. a second inert compressed layer comprising an inert excipient, which is insoluble in gastric fluids but soluble in at least one region of the intestine, wherein the inert excipient is present in amounts such that the inert compressed layer retains its size at least until coated tablet is emptied from the stomach.

BRIEF DESCRIPTION OF THE DRAWINGS

Many aspects of the invention can be better understood with reference to the following figures. The figures only represent one of the embodiments of the present invention. The embodiments are meant only for the purpose of illustration of the present invention. The components in the drawings are not necessarily to scale, emphasis instead being placed upon clearly illustrating the principles of the present invention.

DETAILED DESCRIPTION OF PARTICULAR EMBODIMENTS

Figure 1:
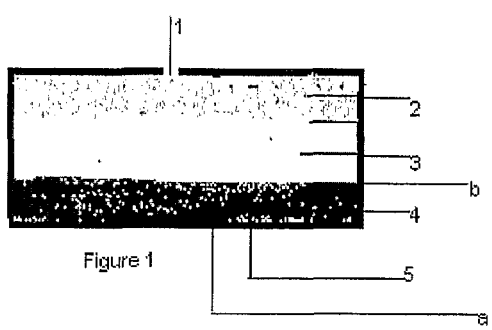
FIG. 1 represents a cross-section view of an embodiment of the present invention wherein a coated tablet is in the form of a trilayer.

Different parts of one of the embodiments of coated tablet of the present invention are given in FIG. 1 and are labeled and the labeling is described herein below
1. passageway
2. Swellable compressed layer
3. Composition in the form of compressed layer comprising therapeutically active ingredient
4. second inert compressed layer
5. Coating having a coat rupturing system
6. Aqueous environment, arrow marks depicting permeation of water through the passageway
(a) external surface of the inert compressed layer
(b) internal surface of the inert compressed layer The term 'external surface' of the inert compressed layer herein means surfaces that are separated from the environment only by the coating and do not adjoin any other composition and the term 'internal surface' herein means the surface that adjoins another composition.

FIG. 1 represents one embodiment of the present invention wherein coated tablet is in the form of a trilayer. The three layers are planar layers.

These layers are described as follows:

A swellable compressed layer (2), active ingredient composition layer (3) and second inert compressed layer (4). The external surface (a) and an internal surface (b) of the inert compressed layer are shown.

The trilayer tablet core is coated with a coating (5). The coating is a defective or a reactive coating as described in our co-pending application WO2005/039481. The coating together with a swellable layer forms a coat rupturing system. It also forms a cup to hold the inert compressed layer. Together they form a reliable means of retaining rigidity and size along one dimension.

In the embodiment of the present invention described in the figures, the coat rupturing system comprises a laser-drilled passageway on the coating and a swellable compressed layer. The passageway is created on the surface of the coating in the immediate vicinity of the swellable compressed layer. Upon contact of coating with water, water enters through the passageway and the swellable compressed layer swells. It exerts pressure on the coating surface having a passageway and the coating ruptures from that surface only while remaining intact on other surfaces. Thus, upon contact with aqueous environment, the coating gets ruptured leaving the coated tablet in the form of a cup from which the active ingredient is released. FIG. 2 to FIG. 5 represent different stages of the mechanism by which the active ingredient is released in a desired manner.

Figure 2:
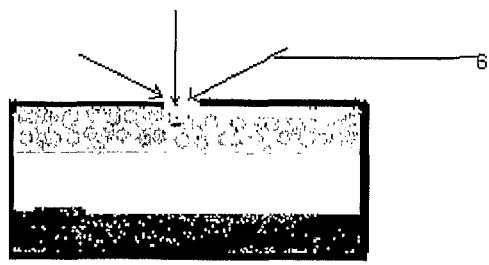
FIGS. 2 to 5 represent views corresponding to FIG. 1 at different stages of the mechanism by which the active ingredient is released in a desired manner.

FIG. 2 represents the stage where the coated tablet comes in contact with the aqueous environment. Upon contact with the aqueous environment (6), there is a rapid ingress of water through the drilled passageway.

Figure 3:
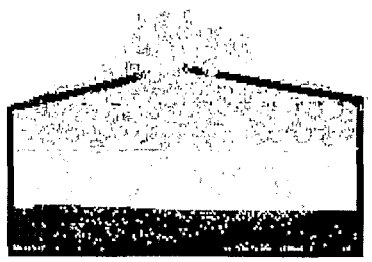

FIG. 3 represents next stage where upon contact with aqueous environment, the swellable compressed layer swells rapidly. The swelling of the excipients exerts a pressure surface of coating having one or more passageways. This leads to opening of the tablet from one surface leaving the tablet in the form of a cup.

Figure 4:
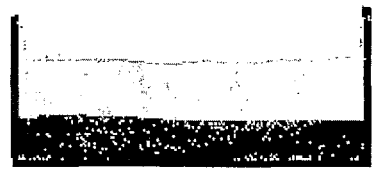

FIG. 4 represents the stage where the swellable compressed layer is completely eroded or disintegrated leaving the active ingredient layer exposed to the aqueous environment. Depending on the nature of the excipients in the active ingredient composition compressed layer, the active ingredient is then released for a desired period of time.

Figure 5:

FIG. 5 describes a stage after the substantially complete release of the active ingredient from the active ingredient compressed layer. The second inert compressed layer is exposed to the aqueous environment after the active ingredient layer has eroded or disintegrated. The second inert compressed layer starts eroding in the intestine causing the coated tablet in the form of cup to collapse.

The present invention provides a coated tablet having prolonged gastric retention comprising
A. a core comprising two or more compositions in the form of compressed layers wherein at least one composition comprises a therapeutically active ingredient and rate controlling excipients
B. a coat rupturing system comprising
  1. one of aforesaid composition in the form of a swellable compressed layer comprising a swelling excipient
  2. a coating comprising a film former, adjoining said swellable compressed layer and surrounding said core, wherein the coating ruptures from at least one of the surfaces when the coated tablet is in an aqueous environment
C. a second inert compressed layer comprising an inert excipient which is insoluble in gastric fluids but soluble in at least one region of the intestine, wherein the inert excipient is present in amounts such that the inert compressed layer retains its size at least until coated tablet is emptied from the stomach.

The coated tablet according to the present invention is such that at least one of the dimension i.e. length or breath or thickness of the tablet is more than 15 mm. The tablet retains the initial size at least along one dimension of the tablet, whereas in the remaining dimensions the size decreases as the pharmaceutical excipients and/or therapeutically active ingredient are released from the system.

Upon contact with the gastric environment, the coating on one of the surfaces ruptures, leaving the tablet in the form of a cup from which the active ingredient is released in a controlled manner from the exposed surface while size along other sides is maintained. Control on the rate of release of active ingredient is obtained because after the coating ruptures from one surface, substantially only that surface with a defined surface area is available for release of the active ingredient. In preferred embodiments, the cup shaped coat that is retained is impermeable. In other embodiments, release of active ingredient by permeation through the coating is only a small proportion of the overall release of the active ingredient.

The core of the coated tablet of the present invention comprises two or more compositions in the form of compressed layers wherein at least one composition comprises one or more therapeutically active ingredients.

The therapeutically active ingredients that may be used in the coated tablets of the present invention may be used include, but are not limited to, alcohol abuse preparations, active ingredients used for Alzheimer's disease, anaesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, steroids and hormones.

According to one embodiment of the present invention, the composition comprising the therapeutically active ingredient itself is divided into number of layers and fabricated using conventional multilayer tableting presses. The individual sub layers may be varied in number and thickness, and each layer may have varying concentrations of the same or different active ingredients to provide the desired delivery profile(s) of the active ingredient(s). This embodiment is particularly useful in providing an ascending release profile i.e the active ingredient is released slowly initially, but as the active ingredient continues to release, the rate of release of the active ingredient increases.

The composition comprising therapeutically active ingredient may comprise pharmaceutically acceptable excipients, which control the release. Such excipients are herein after referred to as "rate controlling excipients". These rate controlling excipients used in the present invention may be selected from hydrophilic polymers such as methyl cellulose, hydroxypropyl methylcellulose, hydroxyethyl cellulose, hydroxypropyl cellulose, hydroxyethyl methylcellulose, carboxymethylcellulose and sodium carboxymethylcellulose; hydrophobic compounds such as ethyl cellulose, glycerol palmitostearate, beeswax, glycowax, castor wax, carnauba wax, glycerol monostearate, stearyl alcohol, glycerol behenic acid ester, cetyl alcohol, natural and synthetic glycerides, waxes, fatty acids, hydrophobic polyacrylamide derivatives, hydrophobic methacrylic acid derivatives; vinyl pyrrolidone polymers such as polyvinylpyrrolidone and copolymers of vinyl pyrrolidone and vinyl acetate; alkylene oxide homopolymers; gums of plant, animal, mineral or synthetic origin; and mixtures thereof. The rate controlling excipients may be used in an amount ranging from about 2% to about 99% by weight of the composition comprising the active ingredient.

One of the embodiments of the present invention uses hydroxypropylmethylcellulose polymers having viscosity ranging from about 50 to about 25,000 mPa·sec as a rate controlling excipient. Examples of the HPMC that may be used, include, but are not limited to, Methocels K4M, K15M and K100M and the like and mixture thereof. In this embodiment, preferably some or all of the HPMC polymers have a viscosity in the range of from 1000 to 25,000 mPa·sec. Preferably, HPMC having viscosity of 100,000 cps is used. The percentage of the hydroxypropyl methylcellulose may range from about 5% to 50% by weight of the active ingredient composition compressed layer.

The composition comprising the therapeutically active ingredient may additionally comprise conventional excipients such as fillers, lubricants, binders, colorants, disintegrants, preservatives, antioxidants and the like.

In one embodiment of the present invention, the coated tablet comprises a "coat rupturing system" comprising a swellable compressed layer. The swellable compressed layer may optionally comprise one or more active ingredients in pharmaceutical acceptable carrier.

The swellable compressed layer comprises swelling excipients, gas generating agents, wicking agents and mixtures thereof. Preferably the swellable excipient is one that can swell upon imbibing water to at least twice its original volume.

The swellable excipient that may be used may be selected from the group comprising cross linked vinylpyrrolidone polymers such as crospovidone; cellulose and cellulose derivatives such as carboxyalkyl celluloses, low substituted hydroxypropyl cellulose, crosslinked carboxyalkylcellulose and their alkali salts; starch and starch derivatives such as pregelatinized starch, dried starch, sodium starch glycolate; resins such as polacrillin potassium (Amberlite IRP 88) and the like and mixtures thereof.

The swellable excipient is preferably used in an amount ranging from about 5% to about 50% by weight of the swellable compressed layer. Preferably, the swellable excipient that may be used in an amount ranging from about 2% to about 40% by weight of the swellable compressed layer.

Gas generating agents that may be used in the present invention include carbonates such as calcium carbonate, bicarbonates such as sodium or potassium bicarbonate, sulfites such as sodium sulfite, sodium bisulfite, or sodium metabisulfite, and the like. These salts may be used alone or in combination with an acid source as a gas generating couple. The acid source may be an edible organic acid, a salt of an edible organic acid, acidic components such as acrylate polymers, or mixtures thereof. Examples of organic acids that may be used include citric acid, malic acid, succinic acid, tartaric acid, fumaric acid, maleic acid, ascorbic acid, glutamic acid, and their salts, and mixtures thereof.

The swellable compressed layer may further comprise a wicking agent in an amount ranging from about 0.5% to about 90% by weight of the swellable composition. Examples of wicking agents that may be used include, but are not limited to, colloidal silicon dioxide, kaolin, titanium dioxide, fumed silicon dioxide, alumina, sodium lauryl sulfate, low molecular weight polyvinylpyrrolidone, bentonite, magnesium aluminum silicate (Veegum K) and the like and mixtures thereof. Preferably, the wicking agents used in the pharmaceutical composition of the present invention include cellulose and cellulose derivatives, colloidal silicon dioxide, and mixtures thereof.

The swellable compressed layer may comprise diluents having wicking action. In certain embodiments of the present invention co-processed microcrystalline cellulose is used as a wicking agent. The microcrystalline cellulose is co-processed with silicon dioxide, preferably colloidal silicon dioxide. Such a co-processed microcrystalline cellulose (silicified MCC) shows improved compressibility as compared to standard grades of microcrystalline cellulose. The silicified microcrystalline cellulose with varying amounts of silicon dioxide is commercially available under the grand name Prosolv®. Typically the colloidal silicon dioxide content is about 2% w/w. The most preferred embodiments of the present invention use silicified microcrystalline cellulose with 2% w/w of colloidal silicon dioxide. These are available commercially under the brand name Prosolv SMCC® 90 with a median particle size in the region of 90 µm and Prosolv SMCC ® 50 with a median particle size in the region of 50 µm.

According to one embodiment of the present invention, the amount of silicified microcrystalline cellulose that may be used in the present invention may range from about 5% w/w to about 90% w/w, more preferably from about 30% to about 70% and most preferably from about 50% to about 80% by weight of the swellable compressed layer.

The swellable compressed layer may also comprise osmogents in an amount ranging from about 0.5% to about 10% by weight of the swellable compressed layer. Examples of osmogents that, may be used include, but are not limited to, inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like; osmopolymers selected from the group consisting of poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly crosslinked with glyoxal, formaldehyde, glutaraldehyde and having a degree of polymerization from 2,000 to 30,000; poly(ethylene oxide) having a molecular weight from 10,000 to 7,8000,000; acidic carboxy polymers known as carboxypolymethylene or as carboxyvinyl polymers, a polymer consisting of acrylic acid lightly cross-linked with polyallylsucrose and sold tinder the trademark Carbopol®, acidic carboxy polymer having a molecular weight of 200,000 to 6,000,000, including sodium acidic carboxyvinyl hydrogel and potassium acidic carboxyvinyl hydrogel; Cyanamer® polyacrylamide; and the like, and mixtures thereof.

In a more preferred embodiment of the invention, the swellable compressed layer comprises a swellable excipient selected from cross linked polyvinyl pyrrolidone and cross linked carboxy methyl cellulose and a diluent having a wicking action for example, silicified microcrystalline cellulose.

The swellable compressed layer additionally may comprise other excipients such as surfactants, lubricants, and other excipients commonly used in the pharmaceutical art.

In one embodiment of the present invention, the coated tablet comprises a "coat rupturing system" comprising a coating adjoining the said swellable compressed layer and surrounding said core, wherein the coating ruptures from one of its surfaces.

According to the present invention, the coating comprises a film former. The film former may be water insoluble polymer. Alternatively, the film former may be a polymer which is insoluble at pH less than about 4.0 but soluble at pH above 7.0.

Examples of water insoluble polymer that may be used include ethyl cellulose, cellulose acetate, polyvinyl acetate, nitrocellulose, butadiene styrene copolymers, and water insoluble methacrylate copolymers. Preferably, the water insoluble polymer is selected from the group consisting of ethyl cellulose, poly(ethyl acrylate, methyl methacrylate, triethylammonioethyl methacrylate chloride), in a ratio 1:2:0.1, (commercially available under the trade names Eudragit RS100, Eudragit RS PO, Eudragit RS 30D and Eudragit RS 12.5) and poly(ethyl acrylate, methyl methacrylate, trimethylammonioethymethacrylate chloride) in a ratio 1:2:0.2 (commercially available under the trade names Eudragit RL100, Eudragit RL PO, Eudragit RL 30D and Eudragit RL 12.5).

Examples of film formers that are insoluble below a pH of about 4.0 but soluble at pH above 7.0 include poly(methacrylic acid, methyl methacrylate) in a ratio 1:1 (Commercially available under the tradenames Eudragit L 100, Eudragit L 12.5, Eudragit 12.5 P), Poly(methacrylic acid, ethyl acrylate) in a ratio 1:1 (Commercially available under the trade names Eudragit L 30 D-55, Eudragit L 100-55, Eastacryl 30 D, Kollicoat MAE 30 D and Kollicoat MAE 30 DP) and poly (methacrylic acid, methyl methacrylate) in a ratio 1:2 (Commercially available under the trade names Eudragit S 100, Eudragit S 12.5, Eudragit S 12.5 P), cellulose acetate phthalate, hydroxypropyl methyl cellulose acetate succinate and the like and mixture thereof.

In one embodiment of the present invention, the water insoluble polymer included in the coating may be in the form of an aqueous dispersion. For example, aqueous dispersions of any of the aforementioned insoluble polymers may be used. Most preferably, an aqueous dispersion of ethyl cellulose is used.

Suitable aqueous dispersions of ethyl cellulose include those commercially available under the trade names Aquacoat ECD-30® from FMC Corporation (Philadelphia, USA) and Surelease® from Colorcon (West Point, Pa.). Aquacoat® is an aqueous polymeric dispersion of ethylcellulose and contains sodium lauryl sulfate and cetyl alcohol, while Surelease® is an aqueous polymeric dispersion of ethyl cellulose and contains dibutyl sebacate, oleic acid, ammoniated water and fumed silica.

The coat may be applied to a weight gain of about 5% to about 20% by weight, preferably from about 8% to about 15% by weight of the core.

According to the present invention the coat is substantially impermeable to the passage of the active ingredient. Upon contact with the aqueous environment, the coating is ruptured from at least one of its surfaces and thereby release of the active ingredient is enabled. The coat is ruptured from at least one of the surfaces by the action of a coat rupturing system.

The coat rupturing system comprises the swellable compressed layer and the coating, which is defective or reactive as described in our co-pending application W02005/039481. Preferably, the coating that ruptures from at least one of the surfaces is selected from the group consisting of a coating comprising a film former and a pore forming agent, a coating comprising a film former and optionally a plasticizer wherein the type and amounts of the film former and optionally the plasticizer are selected to form a coating capable of rupturing upon swelling of the swellable compressed layer in the core; and a coating comprising a film former and one or more passageways.

When the coating has one or more passageways, they may be created by techniques such as manual, laser drilling and the like. A passageway may be drilled in the vicinity of the swellable compressed layer so that upon contact with aqueous environment, water enters through the drilled passageways, the swellable compressed layer swells and exerts pressure on that surface and eventually ruptures the coating from the drilled surface.

The diameter of the pore is selected such that no substantial delay occurs in rupturing of the coat. Preferably, the pore diameter is in the range from about 500 μm to about 1000 μm. The term "without a substantial delay" as used herein means that the active ingredient release is initiated from the coated tablets of the present invention within 0 to 60 minutes from the time the core contacts an aqueous environment, preferably within 0 to 20 minutes, and most preferably within 0 to 5 minutes.

In another embodiment of the present invention the coating comprises a film former and a pore-forming agent. A pore forming agent may be defined herein as an agent that forms micro porous coatings formed in situ by dissolution upon exposure to an aqueous environment of use. Pores may also be formed in the coating by gas formation. The pore forming agent may be a solid or a liquid. Pore-forming agents that may be used include water-soluble compounds that have molecular weight of less than about 2000 Daltons and hydrophilic polymers.

The pore forming agents that may be used in the present invention may be selected from the group consisting of alkali metal salts, alkaline earth metals, transition metal salts, organic compounds and the like.

The examples of alkali metal salts include, but not limited to, sodium chloride, sodium bromide, sodium carbonate, potassium chloride, potassium sulfate, potassium phosphate, sodium acetate, sodium citrate, potassium nitrate, and the like. Examples of alkaline earth metal salts include, but not limited to, calcium phosphate, calcium nitrate, calcium chloride, and the like. Examples of transition metal salts include, but not limited to, ferric chloride, ferrous sulfate, zinc sulfate, cupric chloride, manganese fluoride, manganese fluorosilicate, and the like. Examples of organic aliphatic oils include, but not limited to, diols and polyols, aromatic oils including diols and polyols, and other polyols such as polyhydric alcohol, polyalkylene glycol, polyglycol and the like.

Examples of organic compounds that may be used as pore forming agent, include, but not limited to, monosaccharides, polysaccharides, sugar alcohol and the like. As used herein, the monosaccharides contain from 3-6 carbon atoms and include aldoses and hexoses. Examples of monosaccharides include glyceraldehydes, erythrose, threose, ribose, arabinose, xylose, allose, altrose, glucose, mannose, galactose, talose, erythrulose, ribulose, xylulose, psicose, fructose, sorbose, tagatose, and the like. The monosaccharides may exist as either the D or L isomer, although the D-isomer is preferred. Examples of disaccharides include maltose, lactose, sucrose and the like. The most preferred pore forming agent used in the coating composition of the present invention is selected from sugar alcohols, most preferably mannitol.

Examples of hydrophilic polymers that may be used as pore forming agents are selected from the group comprising of vinyl polymers, cellulose derivatives, polyethylene glycols and the like and mixtures thereof.

Examples of the vinyl polymers that may be used as pore forming agent include, but are not limited to, polyvinyl pyrrolidone, polyvinyl alcohol and the like and mixtures thereof.

When the polymer is polyvinyl pyrrolidone (PVP) it is preferred that the PVP has an average molecular weight of about 2000 to about 3 million and more preferably from about 7000 to about 1,500,000. Most preferred PVP has an average molecular weight of about 40,000 (such as Povidone K30) or about 1,500,000 (such as Povidone K90). Both Povidone K30 and K90 are commercially available from BASF, Midland, Mich.

Examples of the cellulose derivatives that may be used as hydrophilic polymers include, but are not limited to, methylcellulose, hydroxypropyl cellulose, hydroxypropyl cellulose, hydroxyethyl cellulose and mixtures thereof. Preferably, low viscosity grade cellulose derivatives are used. The low viscosity grade cellulose derivatives that may be used may have a viscosity ranging from about 2 to about 50 mPa. These are the typical viscosity values for 2% (w/v) aqueous solutions measured at 20° C. Examples of low grade viscosity hydroxy propyl methyl cellulose derivatives that may be used include, but not limited to, E3 Low viscosity (LV) grade having viscosity of 2.4 to about 3.6, E5 LV having viscosity of 4 to about 6, E6 having viscosity ranging from 5 to 7, E15having viscosity ranging from 12 to 18; E50 having viscosity ranging from 40 to 60; K3 having viscosity ranging from 2.4 to 3.6 and the like and mixtures thereof. Other cellulose derivatives that may be used include, but not limited to, low substituted hydroxy propyl cellulose (L-HPC), hydroxyethyl cellulose (HEC). HEC is known under the brand name of Natrosol. Hydroxyethyl cellulose is available in a wide range of viscosity types; e.g., Cellosize is manufactured in 11 regular viscosity grades. Hydroxyethyl cellulose grades differ principally in their aqueous solution viscosities which range from about 2 to about 20,000 mPa s for a 2% w/v aqueous solution. Two types of Cellosize are produced, a WP-type, which is a normal-dissolving material, and a QP-type, which is a rapid-dispersing material. Generally, low viscsotiy grades are preferred in the present invention. Examples of low viscosity grade hydroxy ethyl cellulose include, but are not limited to, commercially available grades under the tradenames WP 02 grade, WP 09 grade.

Examples of the polyethylene glycol that may be used include, but are not limited to, polyethylene glycol having average molecular weights ranging from about 1,000 to 6000.

The pore forming agent is present in an amount ranging from about 5% (w/w) of the dry weight of the coating to not more than about 50% of the dry weight of the coating (w/w). More preferably, it is present from about 6% to about 40% of the coating (dry weight) and still more preferably from about 10% to about 20% of the coating (dry weight). In addition, the dry weight ratio of the water insoluble polymer to the pore forming agent ranges from about 1:9 to about 9:1; and even more preferably from about 6:4 to about 4:6 and most preferably from about 7:3 to about 8:2.

In one embodiment of the present invention, the coat rupturing system comprises a coating comprising a film former and optionally a plasticizer wherein the type and amounts of film former and optionally plasticizer are selected to form a coating capable of rupturing upon swelling compressed layer in the core.

The type and amount of plasticizer used in the coating composition may depend upon the type of film forming agent used. The amounts and type are selected to form a coating capable of rupturing upon swelling of the swellable compressed layer in the core. Varying amounts of plasticizers may cause weakness in the coating thereby allowing rupturing of the coat. The low amount of plasticizers may make the coating brittle and therefore susceptible to breaking upon contact with the aqueous environment.

The plasticizers that are used in coating are generally the ones conventionally known in the art. For example, the plasticizers that may used include, but are not limited to, diethylphthalate, triethyl citrate, triethyl acetyl citrate, triacetin, tributylcitrate, polyethylene glycol, glycerol, vegetable and mineral oils, maltodextrin and mixtures thereof, and the like. The plasticizer may be present in the coating in amounts ranging from about 0.01% to about 25% by weight and more preferably from about 5% to about 15% by weight based on the dry weight of the coating.

The coating contains at least about 5% solids with the remainder being water. Preferably, the coating contains from about 5% to about 30% solids and more preferably from about 10% to about 25% by weight of the solids.

Besides the water insoluble polymer, pore forming agent and the water, the coating may also contain other additives normally found in coatings used in the pharmaceutical art. These include plasticizers, wetting agents, lubricants, coloring agents commonly used in the pharmaceutical art.

The coloring agents are added to provide elegance and product distinction. Suitable ingredients for providing color to the formulation include titanium dioxide and color pigments, such as iron oxide pigments, FD&C Yellow No. 6, FD&C Red No. 2, FD&C Blue No. 2, food lakes and the like. If present, they are present in amounts ranging from about 0.1% to about 20% by dry weight of the coating composition (w/w) and more preferably less than about 3% by dry weight (w/w) of the coating.

The coating may optionally include a lubricant. Examples of suitable lubricants include talc, calcium stearate, colloidal silicon dioxide, glycerin, magnesium stearate, aluminum stearate, or a mixture of any two or more of the forgoing, and the like. The lubricant may be present in amounts ranging from about 0.01% to about 10% by dry weight of the coating.

According to the present invention, the coated tablet comprises a second inert compressed layer comprising an inert excipient which is insoluble in gastric fluids but soluble in at least one region of the intestine, wherein the inert excipient is present in amounts such that the inert compressed layer retains its size at least until the coated tablet is emptied from the stomach.

The amount of inert excipient may vary from about 5% to about 90% of the total weight of the second compressed layer, preferably from about 10% to about 50% of the total weight of the second compressed layer.

According to the present invention, the inert excipient is insoluble in gastric fluids but soluble in at least one region of the intestine. In one of the preferred embodiment the inert excipient is pH dependent polymer.

Examples of the pH dependent polymer that may be used include, but are not limited to, cellulose acetate phthalate, hydroxypropyl methylcellulose phthalate, polyvinyl acetate phthalate and polymethacrylate and the like and mixtures thereof.

Examples of polymethacrylate that may be used include, but are not limited to, Eudragit L and S. These are generally referred to as methacrylic acid copolymers and are anionic co polymerization products of methacrylic acid and methyl methacrylate. The ratio of free carboxyl groups to esters is approximately 1:1 in Eudragit L and 1:2 in Eudragit S. Both polymers are readily soluble in neutral to weakly alkaline conditions (pH 6-7) and forms salts with alkalis. These polymers are available as solution with or without plasticizers, free flowing powders with at least 95% of dry polymers.

Another grade of Eudragit polymer is Eudragit L 30 D-55. These are available as an aqueous dispersion of an anionic copolymer based on methacrylic acid and ethyl acrylate. The ratio of free carboxyl groups to ester groups is 1:1. Films prepared from these copolymers dissolve above pH 5.5 forming salts with alkalis, thus affording coating which is insoluble in gastric media, but soluble in the small intestine. Eudragit L 100-55 is a white, free flowing powder, which is redispersible in water to form a latex, which has properties similar to Eudragit L 30 D-55.

According to one embodiment of the present invention, the second inert compressed layer may optionally comprise hydrophobic materials. Examples of the hydrophobic material that may be used include, but are not limited to, glyceryl behenate, hydrogenated castor oil and the like and mixtures thereof.

The coated tablets of the present invention may be any suitable shape, such as round, oval, biconcave, hemispherical or any polygonal shape such as square, rectangular, pentagonal and the like.

The tablet core may be obtained by the conventional processes, such as wet, dry granulation or direct compression. For example, the therapeutically active ingredient composition is prepared first. When the therapeutically active ingredient layer composition is prepared by wet granulation active ingredient is mixed with other pharmaceutically acceptable excipients and granulated, followed by screening and drying of the damp mass. The dried mass may be screened, lubricated and compressed. Dry granulation can be done by two processes: (1) slugging, which involves mixing the active ingredient with other the excipients, slugging, dry screening, lubrication and compression, or (2) roller compaction process. Direct compression involves compressing the physical mixture therapeutically active ingredient with the excipients.

The swellable compressed layer may be prepared by conventional methods known in the pharmaceutical art. For example, the swelling agents, diluents and other additives may be mixed and further processed by either dry, wet granulation or direct compression.

The compositions for example, the therapeutically active ingredient compressed layer and the swellable compressed layer and the inert compressed layer compositions are granulated, the granules of the individual compositions are compressed to form a trilayer tablet using a rotary compression. When the compositions are processed by direct compression, the blends of the compositions respectively, may be compressed using a rotary press.

The coating of the tablet core is carried out by art-recognized techniques. The water insoluble polymer in the aqueous dispersion is either commercially obtained or is prepared using known emulsion polymerization techniques.

In one embodiment of the present invention, the coating is drilled by mechanical means either manual drilling or by laser drilling by techniques known in the art. Optionally, when a pore forming agent is used, a pore-forming agent is mixed with water, if further dilution is desired, and mixed until the pore forming agent is completely dissolved in the coating dispersion. The coating composition may be prepared by dissolving the pore forming agent in water and adding the dispersion of the water insoluble polymer to it, and then mixing the two together until the water soluble compound is dissolved in the aqueous dispersion. Alternatively, the coating dispersion may be prepared by adding water to the dispersion of the water insoluble polymer and then dissolving the pore-forming agent, in the diluted dispersion. Whichever way made, the coating has a solid content ranging from about 5% to about 25% w/w, preferably from about 10% to about 20%, more preferably from about 10% to about 15% w/w.

The following example does not limit the scope of the invention and are used as illustrations.

EXAMPLE

TABLE 1

SWELLABLE COMPRESSED LAYER

| Ingredients | mg per tablet | % w/w of the swellable compressed layer |
|---|---|---|
| Carbidopa mohohydrate equivalent to carbidopa anhydrous | 10.0 | 2.8 |
| Levodopa | 40.0 | 11.4 |
| Silicified Microcrystalline Cellulose (Prosolv SMCC 90) | 212.40 | 60.6 |
| Crospovidone | 60.00 | 17.14 |
| Colloidal silicon dioxide | 7.50 | 2.14 |
| Polyvinyl pyrrolidone | 15.00 | 4.28 |
| FDC Blue No. 1 Lake | 1.20 | 0.34 |
| Magnesium stearate | 2.40 | 0.68 |
| Magnesium stearate | 0.75 | 0.21 |
| Talc | 0.75 | 0.21 |
| Total weight | 350.0 | |

TABLE 2

THERAPEUTICALLY ACTIVE INGREDIENT COMPRESSED LAYER

| Ingredients | mg per tablet | % w/w of the active ingredient compressed layer |
|---|---|---|
| carbidopa | 40.0 | 7.9 |
| levodopa | 160.0 | 31.68 |
| Hydroxypropyl methyl cellulose HPMC K100 Viscosity grade (100,000) * K 100 M | 50.0 | 9.9 |
| Mannitol SD 200 | 206.0 | 40.79 |
| Polyvinyl pyrrolidone K30 | 30.0 | 5.94 |
| Colloidal silicon dioxide | 8.0 | 1.58 |
| Talc | 5.0 | 0.99 |
| Magnesium stearate | 6.0 | 1.18 |
| Total weight | 505.0 | |

TABLE 3

INERT COMPRESSED LAYER

| Ingredients | mg per tablet | % w/w of the inert compressed layer |
|---|---|---|
| Microcrystalline Cellulose (Avicel PH 102) | 224.19 | 63.15 |
| Methacrylate copolymer type C (Eudragit L100 55) | 71.0 | 20 |
| Polyvinyl pyrrolidone K30 | 53.25 | 15 |
| Talc | 2.66 | 0.74 |
| Magnesium stearate | 2.66 | 0.74 |
| FD & C Yellow No. 6 Lake | 1.24 | 0.34 |
| Total weight | 355.00 | |

The active ingredients along with the inactive ingredients are mixed and subjected to slugging. The slugs were mixed with magnesium stearate, talc and compressed.

The weighed amounts of active ingredient were mixed with colloidal silicon dioxide. The blend was sieved and passed through 40 mesh. The blend was mixed with HPMC K100 LV, Mannitol SD200 and PVP K 30 and sifted again. This blend was granulated with purified water in the rotary mixer grinder. The granules were dried and milled and extragranular additives added further.

The pigment and MCC were mixed and sifted through #60. Eudragit L100 55, PVP K30 & remaining qty of MCC were mixed together and sifted through #40. Blend of talc & magnesium stearate was passed through #60. All the blends were mixed together in a double cone blender and mixed for 10 min.

The compositions of all the three layers were used for compression. The compression was performed on a trilayer compression machine at a target weight of about 1210 mg

TABLE 4

COATING

| Ingredients | mg per core tablet of the core | Percent w/w dry weight |
|---|---|---|
| Aquacoat EC30 D* | 77.52 | |
| Ethyl cellulose | 20.93 | 69.21 |
| Sodium lauryl sulphate | 0.7752 | 2.56 |
| Cetyl alcohol | 1.55 | 5.12 |
| Dibutyl sebacate | 5.81 | 19.21 |

TABLE 4-continued

COATING

| Ingredients | mg per core tablet of the core | Percent w/w dry weight |
|---|---|---|
| Triethyl citrate | 1.16 | 3.83 |
| water | 15.15 | |

Aquacoat EC 30 D is the commercially available ethyl cellulose aqueous dispersion containing 27% w/v of ethyl cellulose, 1% SLS and 2% cetyl alcohol.

The trilayer tablet prepared was coated with ethyl cellulose aqueous dispersion to achieve a weight gain of approximately 12% of the weight of the core tablet. The coated tablets were drilled on the surface in the immediate vicinity of the swellable compressed layer.

The approximate size of the coated tablet is 19.4 mm (length), 9.8 mm (breadth) and 9.5 mm in thickness.

When the drilled coated tablets are placed in aqueous medium, the coating ruptured in about 5 minutes to about 10 minutes exposing the therapeutically active ingredient composition to the gastric environment.

The coated tablets were subjected to in vitro dissolution testing in simulated gastric fluids (0.01 N hydrochloric acid) at 100 rpm and 37° C. using Type 1 USP dissolution apparatus.

TABLE 5 in vitro dissolution data for carbidopa and levodopa

| | % released | |
|---|---|---|
| Time in Hours | Carbidopa | levodopa |
| 0 | 0 | 0 |
| 1 | 22 | 24 |
| 2 | 31 | 33 |
| 4 | 52 | 57 |
| 6 | 76 | 82 |
| 8 | 86 | 95 |

The invention claimed is:

1. A coated tablet having prolonged gastric retention comprising:
a core comprising two or more compressed laminar layers, wherein at least one of the layers comprises a therapeutically active ingredient and rate controlling excipients, wherein the rate controlling excipients is selected from methyl cellulose, hydroxypropyl methylcellulose, hydroxyethyl cellulose, hydroxypropyl cellulose, hydroxyethyl methylcellulose, carboxymethylcellulose and sodium carboxymethylcellulose; ethyl cellulose, glycerol palmitostearate, beeswax, glycowax, castor wax, carnauba wax, glycerol monostearate, stearyl alcohol, glycerol behenic acid ester, cetyl alcohol, natural and synthetic glycerides, waxes, fatty acids, hydrophobic polyacrylamide derivatives, hydrophobic methacrylic acid derivatives; vinyl pyrrolidone polymers; alkylene oxide homopolymers; gums of plant, animal, mineral or synthetic origin; and mixtures thereof,
wherein at least one of the layers of the core is a swellable compressed layer comprising at least one of (i) a swelling excipient, wherein the swellable excipient is selected from the group consisting of crospovidone; carboxyalkyl celluloses, low substituted hydroxypropyl cellulose, crosslinked carboxyalkylcellulose and their alkali salts; pregelatinized starch, dried starch, sodium starch glycolate; resins; and mixtures thereof, (ii) a gas generating agent selected from the group consisting of calcium carbonate, sodium bicarbonate, potassium bicarbonate, sodium sulfite, sodium bisulfite, sodium metabisulfite, citric acid, malic acid, succinic acid, tartaric acid, fumaric acid, maleic acid, ascorbic acid, glutamic acid, their salts, and mixtures thereof, and (iii) a wicking agent selected from the group consisting of colloidal silicon dioxide, kaolin, titanium dioxide, fumed silicon dioxide, alumina, sodium lauryl sulfate, low molecular weight polyvinylpyrrolidone, bentonite, magnesium aluminum silicate, and mixtures thereof, wherein at least another one of the layers of the core is an inert compressed layer comprising an inert excipient which is insoluble in gastric fluids but soluble in at least one region of the intestine, wherein the inert excipient is selected from a group consisting of cellulose acetate phthalate, hydroxypropyl methylcellulose phthalate, polyvinyl acetate phthalate and polymethacrylate and mixtures thereof, wherein the inert excipient is present in amounts such that a shape and dimensions of the inert compressed layer are maintained at least until the coated tablet is emptied from the stomach, and the inert compressed layer starts eroding in the intestine, and a coating comprising a water insoluble film former adjoining said swellable compressed layer and said inert compressed layer, said water insoluble film former surrounding said core, wherein said coating has a plurality of surfaces including (i) a first surface and (ii) other surfaces forming a cup containing the inert compressed layer, wherein an external surface of the inert compressed layer adjoins the coating and an internal surface of the inert compressed layer adjoins the layer comprising the therapeutically active ingredient and rate controlling excipients, wherein said swellable compressed layer and said coating form a coat rupturing system such that, upon swelling of the swellable compressed layer, the coating ruptures from at least the first surface when the coated tablet is in an aqueous environment, leaving the cup containing the inert compressed layer, so that the active ingredient is released in a controlled manner from an exposed surface of the layer comprising the therapeutically active ingredients and rate controlling excipients, while a shape of the cup is maintained.

2. A coated tablet as claimed in claim 1 wherein at least one dimension of the tablet among length dimension, width dimension and thickness dimension is more than 15 mm.

3. A coated tablet as claimed in claim 1 wherein the coating that ruptures from at least one of the surfaces is selected from the group consisting of:
   a. a coating comprising a film former and a pore forming agent;
   b. a coating comprising a film former and optionally a plasticizer wherein the type and amounts of the film former and optionally the plasticizer are selected to form a coating capable of rupturing upon swelling of the swellable compressed layer in the core; and
   c. a coating comprising a film former and one or more passageways.

4. A coated tablet as claimed in claim 1 wherein the coating is impermeable to the active ingredient.

5. A coated tablet as claimed in claim 1 wherein the film former comprises a water insoluble polymer and the water insoluble polymer is selected from the group comprising ethyl cellulose, nitrocellulose, polyvinyl acetate and mixtures thereof.

6. A coated tablet as claimed in claim 5 wherein the water insoluble polymer comprises ethyl cellulose and the ethyl cellulose is applied to a weight gain ranging from about 8% to about 15% by weight of the core.

7. A coated tablet as claimed in claim 1 wherein the swellable compressed layer comprises swelling excipients, gas generating agents, wicking agents and mixtures thereof.

8. A coated tablet as claimed in claim 1, wherein the rate controlling excipients is a vinyl pyrrolidone polymer selected from polyvinylpyrrolidone and copolymers of vinyl pyrrolidone and vinyl acetate, and mixtures thereof.

9. A coated tablet as claimed in claim 1, wherein the swellable excipient is a resin selected from the group consisting of polacrillin potassium and mixtures thereof.

10. A coated tablet as claimed in claim 1, wherein the coating comprises a preformed passageway or pore formers.

\* \* \* \* \*